US010658912B2

(12) United States Patent
Lin et al.

(10) Patent No.: US 10,658,912 B2
(45) Date of Patent: May 19, 2020

(54) SHOCK WAVE GENERATING UNIT (71) Applicant: LITE-MED INC., Taipei (TW)

(72) Inventors: Chia-Chi Lin, Taipei (TW);
Yung-Chen Su, Taipei (TW);
Po-Hsiang Kuo, Taipei (TW)

(73) Assignee: Lite-Med Inc., Taipei (TW)

( * ) Notice: Subject to any disclaimer, the term of this patent is extended or adjusted under 35 U.S.C. 154(b) by 519 days.

(21) Appl. No.: 15/475,727

(22) Filed: Mar. 31, 2017

(65) Prior Publication Data
US 2018/0287465 A1    Oct. 4, 2018

(51) Int. Cl.
*H02K 33/16*        (2006.01)
*A61B 17/225*       (2006.01)
*G10K 9/13*         (2006.01)

(52) U.S. Cl.
CPC .......... *H02K 33/16* (2013.01); *A61B 17/225* (2013.01); *G10K 9/13* (2013.01)

(58) Field of Classification Search
CPC ........ H02K 33/16; H02K 33/00; H02K 35/00; H02K 1/34; H02K 9/19; G10K 9/12; G10K 9/13; A61B 17/225
USPC .............. 310/15–17, 21, 25, 29, 32, 36; 601/78–80; 367/175
See application file for complete search history.

(56) References Cited

U.S. PATENT DOCUMENTS

| | | | | |
|---|---|---|---|---|
| 4,718,421 A | * | 1/1988 | Rohwedder | G10K 11/30 310/325 |
| 4,823,110 A | * | 4/1989 | Dorward | G10K 9/18 116/142 R |
| 4,901,709 A | * | 2/1990 | Rattner | G10K 9/12 367/175 |
| 4,905,675 A | * | 3/1990 | Oppelt | G10K 9/12 601/4 |

(Continued)

FOREIGN PATENT DOCUMENTS

| | | | | |
|---|---|---|---|---|
| CN | 2422941 Y | * | 3/2001 | |
| DE | 3506583 A1 | * | 8/1986 | ......... A61B 17/225 |
| DE | 4038651 A1 | * | 6/1992 | ............... G10K 9/12 |

OTHER PUBLICATIONS

DE-4038651-A1 (English Translation) (Year: 1992).*
DE-3506583-A1 (English Translation) (Year: 1986).*
CN-2422941-Y (English Translation) (Year: 2001).*

*Primary Examiner* — Alfonso Perez Borroto
*Assistant Examiner* — Alexander Moraza
(74) *Attorney, Agent, or Firm* — Rosenberg, Klein & Lee (57) ABSTRACT

A shock wave generating unit includes a housing and a disk in the housing. The disk includes a vibration plate, which corresponds to a shock wave transmission member covering a first opening of the housing and includes an insulating thin elastic plate and a thin metal plate. The insulating thin elastic plate, with one side corresponding to the shock wave transmission member and the opposite side provided with the thin metal plate, has a hollow portion for partially exposing the thin metal plate and forms an accommodating cavity (Continued)

together with the exposed portion of the thin metal plate and the shock wave transmission member. A shock wave transmission medium can circulate through the accommodating cavity via a channel in the housing and is in contact with the exposed portion of the thin metal plate to facilitate dissipation of the heat generated by the disk during operation.

9 Claims, 7 Drawing Sheets

(56) References Cited

U.S. PATENT DOCUMENTS 5,374,236 A * 12/1994 Hassler .................... G10K 9/12
367/175

* cited by examiner

SHOCK WAVE GENERATING UNIT

BACKGROUND OF THE INVENTION

1. Technical Field

The present invention relates to a shock wave generating unit and more particularly to one with a thin metal plate in contact with a shock wave transmission medium to facilitate heat dissipation.

2. Description of Related Art

As is well known in the art, shock waves can be put to medical use, such as in lithotripsy for fragment stones in the urinary system. Apart from that, extracorporeal shock wave treatments are a new, non-invasive form of medical care by which high-energy shock waves are applied to an area in chronic pain to promote regeneration of blood vessels, and consequently tissue regeneration and repair, with a view to pain relief. Such treatments are known to be used in treating adhesive capsulitis (generally referred to as frozen shoulder), lateral epicondylitis (tennis elbow), plantar fasciitis (jogger's heel), and so on.

As for shock wave generators, one example is Taiwan Utility Model Patent No. M260235, which, entitled "Structural Improvement on Electromagnetic Shock Wave Generator" and granted to the inventor of the present invention, discloses a shock wave generator including a module fixing base, a focusing biconcave lens, a lens fixing frame, and an disk. The disk is sequentially provided with an insulating base made of alumina, a high-voltage coil, a Teflon connecting membrane, a metal membrane, and a rubber membrane. When an electric current is supplied to the high-voltage coil, a magnetic field is generated and drives the metal membrane in the shallow groove of the rubber membrane into vibration. Consequently, shock waves are produced in the water and are focused by the focusing biconcave lens in order to serve the intended medical purpose.

Shock wave generators required for different treatments vary in size, and those of relatively small sizes are particularly prone to heat dissipation issues.

BRIEF SUMMARY OF THE INVENTION

To address the heat dissipation issues of the prior art, the inventor of the present invention conducted extensive research and experiment and finally succeeded in developing a shock wave generating unit as disclosed herein. The shock wave generating unit includes a housing and a disk. The housing defines a receiving space therein and is provided with a first opening in communication with the receiving space, a shock wave transmission member covering the first opening, and a channel also in communication with the receiving space. The disk lies in the receiving space and is provided at the housing. The disk includes a vibration plate fixedly provided at a position facing the shock wave transmission member. The vibration plate includes an insulating thin elastic plate and a thin metal plate. The insulating thin elastic plate has one side corresponding to the shock wave transmission member and the opposite side provided with the thin metal plate. The insulating thin elastic plate is provided with a hollow portion for exposing a portion of the thin metal plate. The insulating thin elastic plate, the exposed portion of the thin metal plate, and the shock wave transmission member form an accommodating cavity there between. The accommodating cavity is filled with a shock wave transmission medium, which can circulate via the channel and is in contact with the exposed portion of the thin metal plate to facilitate dissipation of the heat generated by the disk during operation.

Preferably, the hollow portion is a plurality of holes.

Preferably, the hollow portion is a hole at the center of the insulating thin elastic plate.

Preferably, the insulating thin elastic plate is ring-shaped and is protrusion provided with a plurality of lugs extending toward a central opening of the insulating thin elastic plate.

Preferably, the shock wave transmission medium is water.

Preferably, the thin metal plate is coated with an insulating film.

Preferably, the disk further includes an insulating base and a coil. The insulating base is provided with two wiring holes. The coil is provided at the insulating base and has two ends extending through the two wiring holes respectively. When supplied with electricity, the coil generates a magnetic field and thereby vibrates the thin metal plate of the vibration plate.

Preferably, the housing further includes a surrounding wall, a base, and an annular cover. The surrounding wall defines the first opening and a second opening opposite the first opening. The base is detachably coupled to the second opening. The annular cover fixes the shock wave transmission member to the surrounding wall such that the first opening is sealed.

Preferably, the periphery of the insulating thin elastic plate is tightly connected to the surrounding wall.

The foregoing technical features can produce the following effects:

1. The portion of the thin metal plate that is exposed through the hollow portion of the insulating thin elastic plate is in contact with the shock wave transmission medium and can therefore rapidly dissipate the heat generated by the disk during operation to increase heat dissipation efficiency.

2. The shock wave transmission medium can circulate via the channel and thereby carry the heat generated during operation away from the shock wave generating unit.

3. The thin metal plate can be coated with an insulating film for more effective insulation.

DETAILED DESCRIPTION OF THE INVENTION

The present invention incorporates the technical features described above into a shock wave generating unit, whose major effects are detailed below with reference to some illustrative embodiments.

Figure 1:
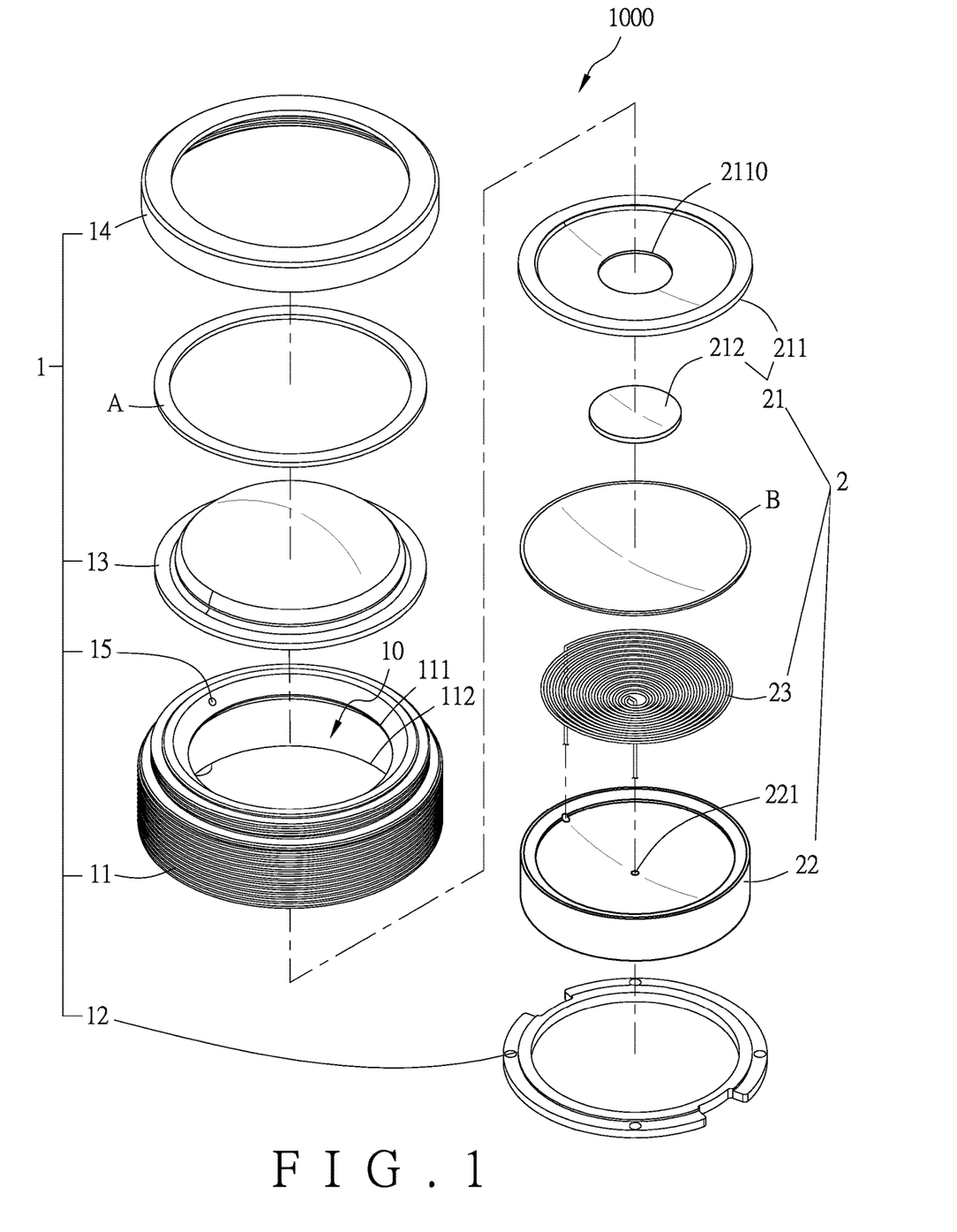
FIG. 1 is an exploded perspective view of the shock wave generating unit in an embodiment of the present invention.
Figure 2:
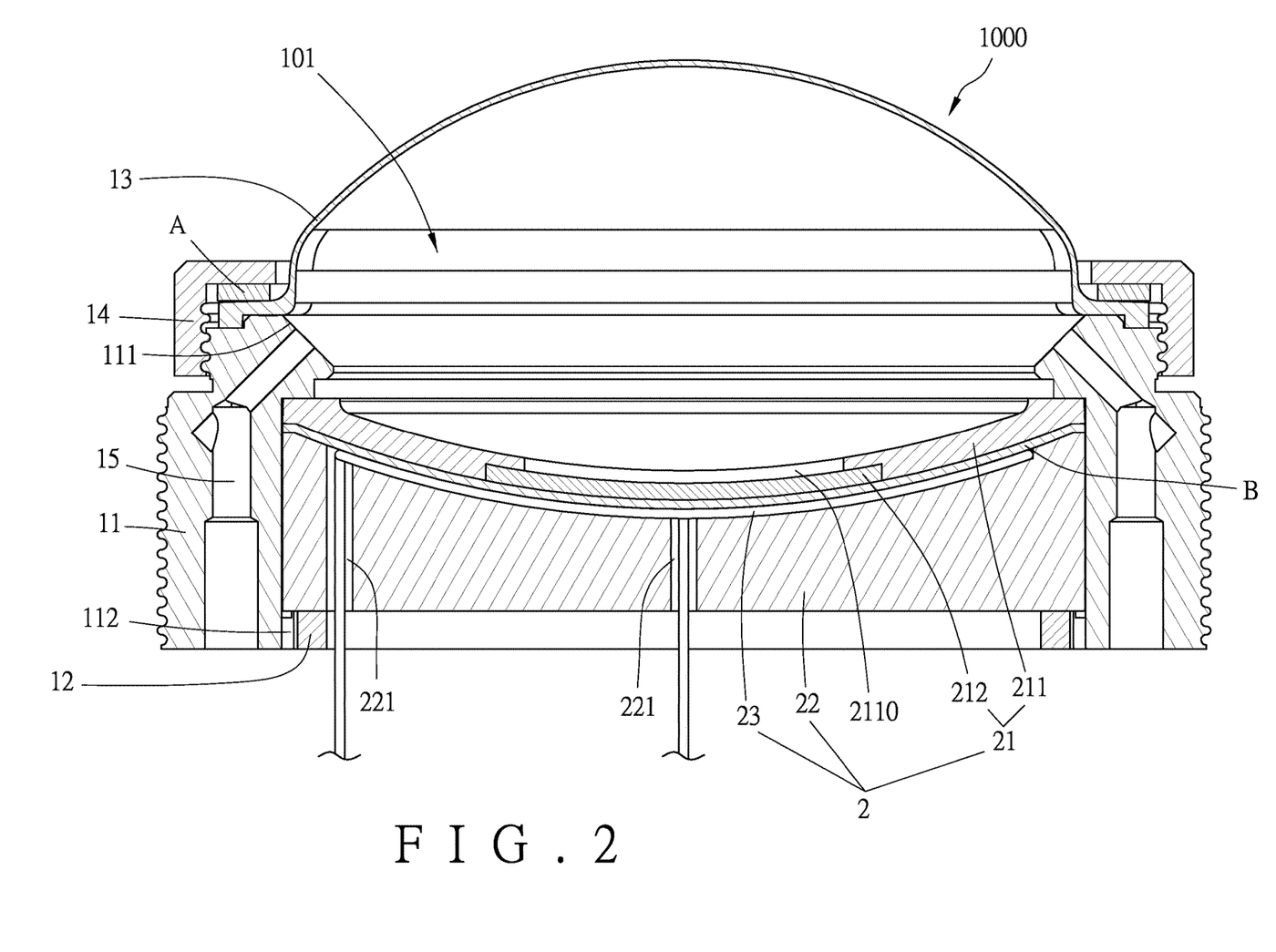
FIG. 2 is an assembled sectional view of the shock wave generating unit in FIG. 1.

As shown in FIG. 1 and FIG. 2, the shock wave generating unit 1000 in an embodiment of the present invention includes a housing 1 and a disk 2. The housing 1 includes a surrounding wall 11, a base 12, a shock wave transmission member 13, and an annular cover 14. The surrounding wall 11 defines a first opening 111 and a second opening 112 opposite the first opening 111. The base 12 is detachably coupled to the second opening 112. The annular cover 14 fixes the shock wave transmission member 13 to the surrounding wall 11 such that the first opening 111 is covered by the shock wave transmission member 13 with the assistance of a sealing ring A. The surrounding wall 11, the base 12, and the shock wave transmission member 13 jointly define a receiving space 10. The housing 1 is further provided with a channel 15 in communication with the receiving space 10. The channel 15 is also in communication with an external circulation system (not shown).

With continued reference to FIG. 1 and FIG. 2, the disk 2 lies in the receiving space 10 and is provided at the housing 1. The disk 2 includes a vibration plate 21 fixedly provided at a position facing the shock wave transmission member 13. The vibration plate 21 includes an insulating thin elastic plate 211 and a thin metal plate 212. One side of the insulating thin elastic plate 211 corresponds to the shock wave transmission member 13 while the opposite side of the insulating thin elastic plate 211 is provided with the thin metal plate 212. In this embodiment, the periphery of the insulating thin elastic plate 211 is tightly connected to the surrounding wall 11. Additionally, the insulating thin elastic plate 211 is provided with a hollow portion 2110, through which a portion of the thin metal plate 212 is exposed. The insulating thin elastic plate 211, the exposed portion of the thin metal plate 212, and the shock wave transmission member 13 jointly form an accommodating cavity 101 there between. The disk 2 further includes an insulating base 22 and a coil 23. The insulating base 22 is made of alumina and is provided with two wiring holes 221. The coil 23 is provided at the insulating base 22 and has two ends extending through the two wiring holes 221 respectively. Furthermore, an insulating layer B covers the coil 23 such that the coil 23 is sandwiched between the insulating base 22 and the insulating layer B and is thus better insulated from its surroundings.

Figure 3:
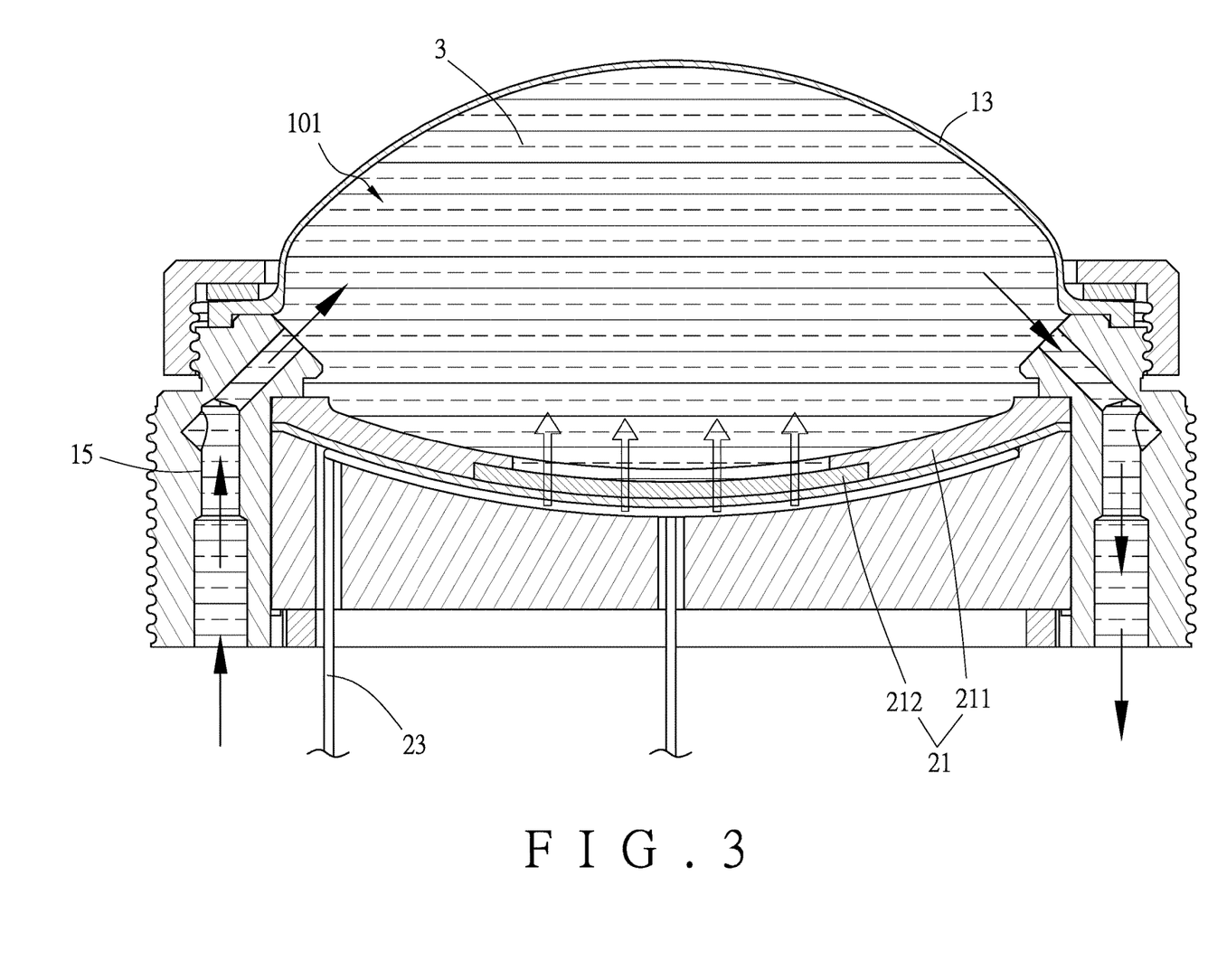
FIG. 3 is another assembled sectional view of the shock wave generating unit in FIG. 1, showing that a shock wave transmission medium is introduced into the shock wave generating unit via a channel, is in contact with the exposed portion of a thin metal plate, and subsequently carries away the heat generated during operation.

Referring to FIG. 3, the accommodating cavity 101 is filled with a shock wave transmission medium 3, which can circulate through the accommodating cavity 101 via the channel 15. When the coil 23 is supplied with an electric signal, a change in magnetic field takes place; as a result, the thin metal plate 212 of the vibration plate 21 is vibrated while supported by the insulating thin elastic plate 211 and generates shock waves. The shock waves propagate outward through the shock wave transmission medium 3 (e.g., water) and the shock wave transmission member 13 (e.g., silicone) in order to be used, for example, in an extracorporeal shock wave treatment.

With continued reference to FIG. 3, the coil 23 tends to accumulate heat when supplied with electricity. Moreover, the size of the shock wave generating unit in this embodiment may vary with the particular shock wave treatment to be performed, and the smaller the shock wave generating unit, the more susceptible it is to damage by the heat accumulated during operation. In this embodiment, the shock wave transmission medium 3 in the accommodating cavity 101 is in contact with the exposed portion of the thin metal plate 212 in order for the thin metal plate 212 to rapidly remove the heat generated during operation. Also, circulation of the shock wave transmission medium 3 through the channel 15 helps dissipate heat from the shock wave generating unit 1000 to protect the expensive shock wave generating unit from damage.

Figure 4:
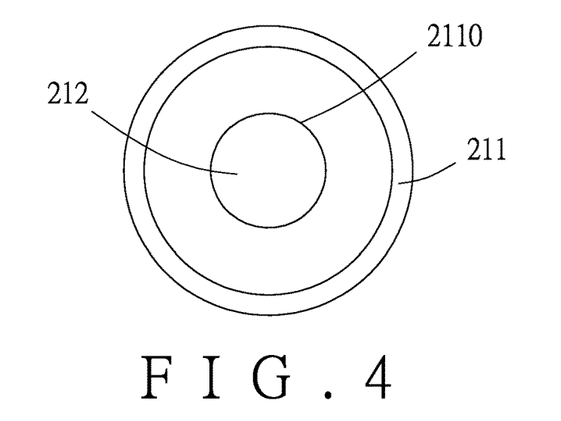
FIG. 4 schematically shows that the insulating thin elastic plate in FIG. 1 is formed with a central hole as its hollow portion.
Figure 5:
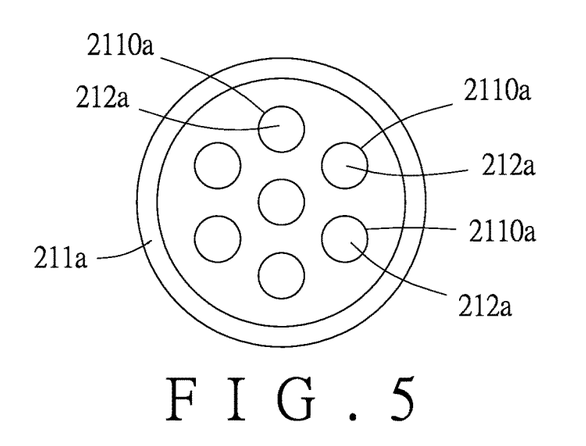
FIG. 5 schematically shows that the insulating thin elastic plate in another embodiment of the present invention is formed with a plurality of holes as its hollow portion.
Figure 6:
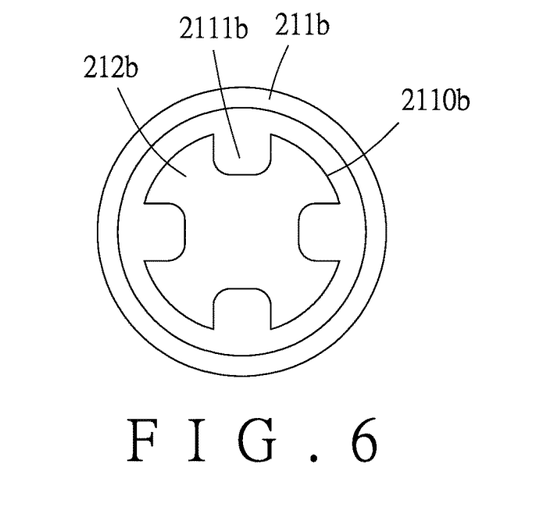
FIG. 6 schematically shows that the insulating thin elastic plate in still another embodiment of the present invention is ring-shaped and is protrusion provided with a plurality of lugs extending toward a central opening of the insulating thin elastic plate to form the hollow portion.

Referring to FIG. 4, the insulating thin elastic plate 211 in this embodiment is formed with a hole at the center, and the hole serves as the hollow portion 2110 for partially exposing the thin metal plate 212. In another embodiment as shown in FIG. 5, the insulating thin elastic plate 211*a* is formed with a plurality of holes as the hollow portion 2110*a* for partially exposing the thin metal plate 212*a*. In still another embodiment as shown in FIG. 6, the insulating thin elastic plate 211*b* is ring-shaped, is protrusion provided with a plurality of lugs 2111*b* extending toward its central opening, and thus also defines the hollow portion 2110*b* for partially exposing the thin metal plate 212*b*. In each of these three embodiments, the thin metal plate 212, 212*a*, or 212*b* is supported by the corresponding insulating thin elastic plate 211, 211*a*, or 211*b* and is therefore enabled to vibrate. Furthermore, the thin metal plate 212, 212*a*, or 212*b* is partially in contact with the shock wave transmission medium through the corresponding hollow portion 2110, 2110*a*, or 2110*b* in order to dissipate heat. For better insulation, the thin metal plate 212, 212*a*, or 212*b* may be coated with an insulating film; the present invention has no limitation in this respect.

Figure 7:
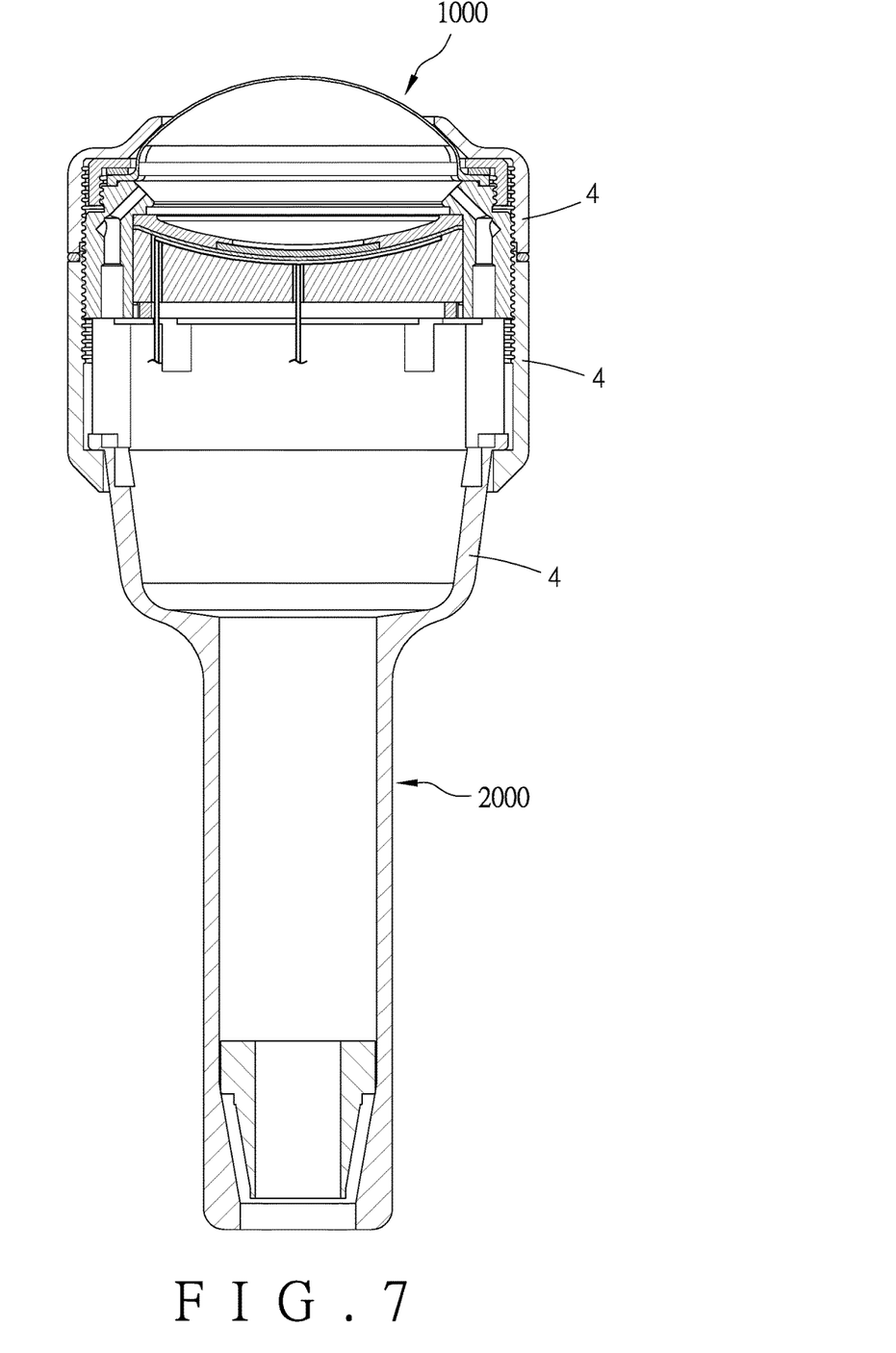
FIG. 7 is a sectional view showing that the shock wave generating unit in FIG. 1 can be coupled with an appropriate casing to form a shock wave generating device with a handle portion.

FIG. 7 shows that the shock wave generating unit 1000 in the first embodiment can be coupled with an appropriate casing 4 to form a shock wave generating device with a handle portion 2000.

Figure 8:
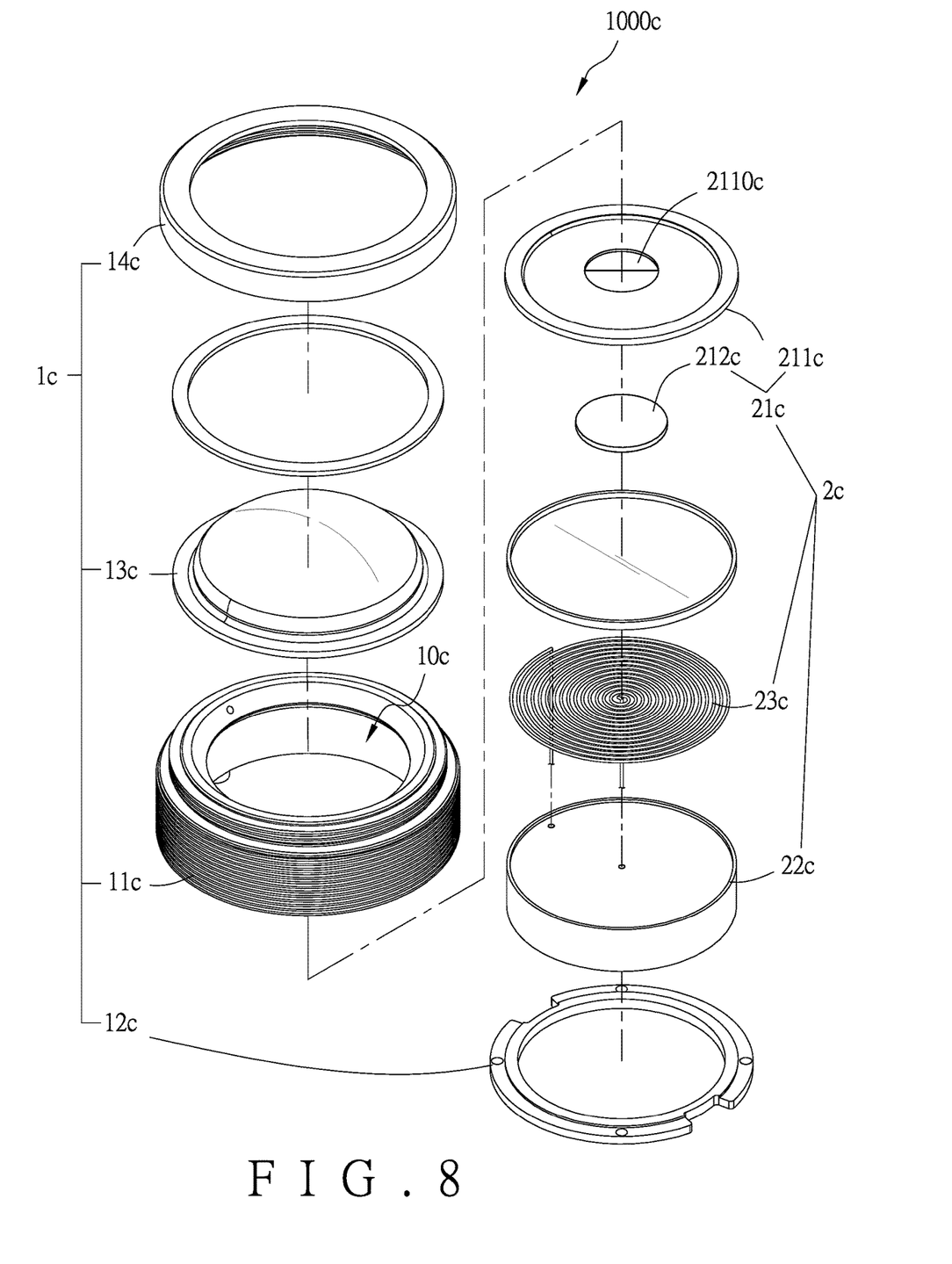
FIG. 8 is an exploded perspective view of the shock wave generating unit in yet another embodiment of the present invention.
Figure 9:
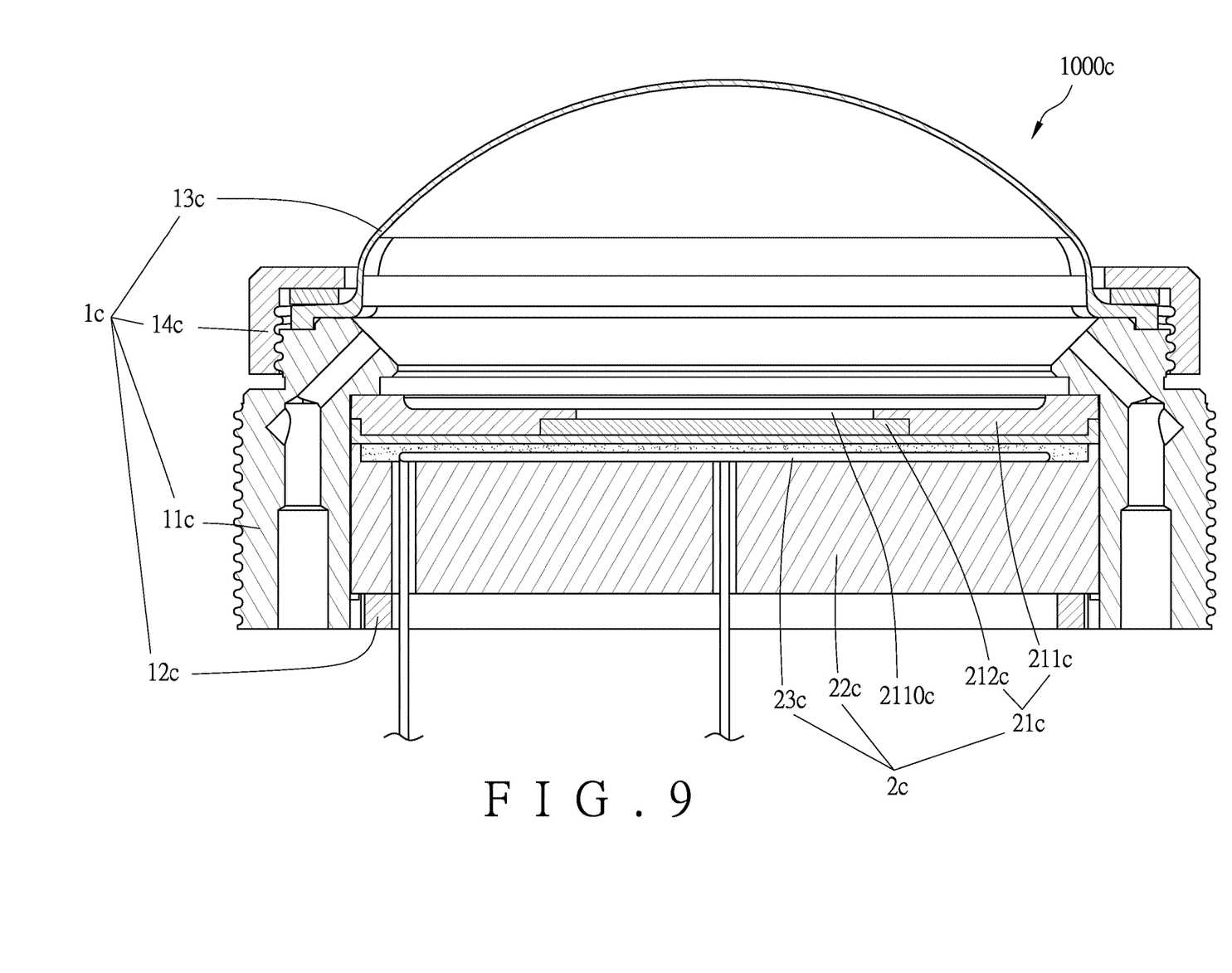
FIG. 9 is an assembled sectional view of the shock wave generating unit in FIG. 8.

In another embodiment of the present invention as shown in FIG. 8 and FIG. 9, the shock wave generating unit 1000*c* is similar in structure to its counterparts in the foregoing embodiments in that it also includes the housing 1*c* and the disk 2*c*; that the housing 1*c* also includes the surrounding wall 11*c*, the base 12*c*, the shock wave transmission member 13*c*, and the annular cover 14*c*; that the disk 2*c* also lies in the receiving space 10*c*, is provided at the housing 1*c*, and includes the vibration plate 21*c*, the insulating base 22*c*, and the coil 23*c*; that the vibration plate 21*c* also includes the insulating thin elastic plate 211*c* and the thin metal plate 212*c*; and that the insulating thin elastic plate 211*c* is also provided with the hollow portion 2110*c*, the difference being that both the insulating thin elastic plate 211*c* and the thin metal plate 212*c* are flat. The shock wave generating unit 1000*c* is equally capable of generating shock waves and also features heat dissipation through the portion of the thin metal plate 212*c* that is exposed through the hollow portion 2110*c*.

Those of ordinary skill in the art who have read the above description of the embodiments should be able to fully understand the operation, use, and effects of the present invention. The embodiments disclosed herein, however, are only some preferred ones of the invention and are not intended to be restrictive of the scope of the invention. All simple equivalent changes and modifications made according to this specification and the appended claims should fall within the scope of the present invention.

What is claimed is:

1. A shock wave generating unit, comprising:
   a housing defining a receiving space therein, wherein the housing is provided with a first opening in communication with the receiving space, a shock wave transmission member covering the first opening, and a portion of the housing having formed therein a channel in communication with the receiving space; and
   a disk disposed in the receiving space within the housing, the disk including:
      a vibration plate fixedly provided at a position facing the shock wave transmission member, the vibration plate including both an insulating thin elastic plate and a thin metal plate, the insulating thin elastic plate having one side facing the shock wave transmission member and an opposite side facing away from the shock wave transmission member, the thin metal plate being coupled to the opposite side of the insulating thin elastic plate to extend across a hollow portion formed therethrough, a portion of the thin metal plate being exposed through the hollow portion to communicate with an accommodating cavity defined between the insulating thin elastic plate and the shock wave transmission member,
   wherein the accommodating cavity is filled with a shock wave transmission medium, and the shock wave transmission medium is circulated via the channel and contacts the exposed portion of the thin metal plate for dissipation of heat generated by the disk during operation.

2. The shock wave generating unit of claim 1, wherein the hollow portion formed through the insulating thin elastic plate is defined by a plurality of holes.

3. The shock wave generating unit of claim 1, wherein the hollow portion formed through the insulating thin elastic plate is defined by a hole at a center of the insulating thin elastic plate.

4. The shock wave generating unit of claim 1, wherein the insulating thin elastic plate includes a ring-shaped outer portion and an inner protrusion portion defining a plurality of lugs extending therefrom toward a central opening of the insulating thin elastic plate.

5. The shock wave generating unit of claim 1, wherein the shock wave transmission medium is water.

6. The shock wave generating unit of claim 1, wherein the thin metal plate is coated with an insulating film.

7. The shock wave generating unit of claim 1, wherein the disk further includes an insulating base and a coil, the insulating base is provided with two wiring holes, the coil is provided at the insulating base and has two ends extending through the two wiring holes respectively, and when supplied with electricity, the coil generates a magnetic field and thereby vibrates the thin metal plate of the vibration plate.

8. The shock wave generating unit of claim 1, wherein the housing further includes a surrounding wall, a base, and an annular cover; the surrounding wall defines the first opening and a second opening opposite the first opening; the base is detachably coupled to the second opening; and the annular cover fixes the shock wave transmission member to the surrounding wall such that the first opening is sealed.

9. The shock wave generating unit of claim 8, wherein the insulating thin elastic plate has a periphery tightly connected to the surrounding wall.

* * * * *